United States Patent [19]

Wilmore

[11] Patent Number: 5,089,475
[45] Date of Patent: Feb. 18, 1992

[54] TREATMENT OF VENTILATOR DEPENDENCY WITH GROWTH HORMONE

[75] Inventor: Douglas W. Wilmore, Brookline, Mass.

[73] Assignee: Brigham and Women's Hospital, Boston, Mass.

[21] Appl. No.: 306,978

[22] Filed: Feb. 7, 1989

[51] Int. Cl.$^5$ .................. A61K 37/02; A61K 37/36
[52] U.S. Cl. .................. 514/12; 514/924; 514/926; 514/885
[58] Field of Search .................. 514/12, 924, 926, 885

[56] References Cited

U.S. PATENT DOCUMENTS 4,863,901 9/1989 Wilmore .................. 514/12

OTHER PUBLICATIONS

Sucher et al., *Anesthesiology* 69:A421 (1988).
Ziegler, T. R., et al., *Ann. Surg.* 208:6–16 (1988).
Williams, T. C. et al., *Pharmacotherapy* 6:311–318 (1986).
Goldstein, S., et al., *Clin. Chest. Med.* 7:141–151 (1986).
Liljedahl, S-O., et al., *Acta Chir. Scand.* 122:1–14 (1961).
Soroff, H. R. et al., *Ann. Surg.* 166:739–752 (1967).
Wilmore, D. W., et al., *Surg. Gyn. Obstet.* 138:875–884 (1974).
Hodgkin, J. A., et al., *Crit. Care Med.* 2:96–102 (1974).
Claus-Walker, J., et al., *J. Clin. Endoc. Metab.* 44:530–535 (1977).
Kelly, S. M. et al., *Am. Rev. Respir. Dis.* 130:33–37 (1984).
Cox, S. A. R., et al., *J. Trauma* 25:419–423 (1985).
Ozturk, et al., *Pharmaceutical Research* 5:550–565 (1988).
Hasegawa et al., *Chem. Pharm. Bull.* 34(5):2183–2190 (1986).
Patel, *Febs Letters* 62:60–63 (1976).
Sanders, S. S., et al., *Brit. Med. J.* 3:25–26 (1969).
Snyder, R. D. et al., *Ann. Allergy* 27:425–428 (1969).
Cornil, A., et al., *Amer. Rev. Resp. Dis.* 112:77–81 (1975).
Gaultier, C., et al., *J. Devel. Physiol.* 8:315–321 (1986).

*Primary Examiner*—F. T. Moezie
*Attorney, Agent, or Firm*—Sterne, Kessler, Goldstein & Fox

[57] ABSTRACT

The invention relates to a method of treating pulmonary dysfunction in a mammal comprising administration of growth hormone to said mammal. In one embodiment wherein the pulmonary dysfunction results in ventilator dependency, the use of the method of this invention promotes the withdrawal of mechanical ventilatory support.

14 Claims, No Drawings

TREATMENT OF VENTILATOR DEPENDENCY WITH GROWTH HORMONE

BACKGROUND OF THE INVENTION

1. Field of the Invention

The invention relates to a method of treating pulmonary dysfunction and dependence on mechanical ventilation in a mammal which comprises administration of growth hormone (GH) to said mammal. In one embodiment the invention pertains to critical care medicine and the treatment of spinal cord injury, chronic obstructive pulmonary disease, and/or sepsis resulting in ventilator dependency. In another embodiment, the invention is directed to improving pulmonary function in other pulmonary diseases, including pneumonia, chronic asthma, emphysema, and tuberculosis.

2. Description of the Background Art

A major problem in critical care medicine is the presence of pulmonary dysfunction. Often, such dysfunction requires that patients be administered mechanical ventilatory support. A further difficulty encountered in such patients is the inability to wean them from ventilators. "Weaning" a patient from ventilatory support ranges from a simple to an extremely complex process. The timing of withdrawal of ventilatory support is critical and criteria have been established to aid in this decision (Hodgkin et al., Crit. Care Med. 2:96 (1974)). The optimization of number of factors is considered necessary before weaning is initiated. Such factors include the correction of anemias, low cardiac output, fluid imbalance, arrhythmias, fever, electrolyte abnormalities, infection, and acid-base disturbances. Specific respiratory physiologic parameters are required to indicate adequate mechanical capability: Vital capacity ($>10-15$ ml/kg); forced expiratory volume ($>10$ ml/kg/sec); peak inspiratory pressure ($-20$ to $-30$ cm $H_2O$); and spontaneous resting minute ventilation ($<10$ L/min).

The concomitant use of intermittent mandatory ventilation (IMV) permits patients to increase muscle strength and improve lung function while gradually undergoing the transition.

Despite advances in respiratory management, patients with thoracic injuries, pulmonary infections, neuromuscular disorders, chronic obstructive lung disease or severe debility complicated by sepsis, are often difficult to wean from mechanical ventilatory support. Earlier weaning from such support carries with it a major economic savings due to the high cost of prolonged intensive care.

Pulmonary problems related to the primary disease are complicated by catabolic responses to infection and injury, muscle wasting following pharmacologic paralysis and bed rest, and the difficulties associated with appropriate nutritional support while maintaining adequate gas exchange (Pingleton et al., J.A.M.A. 257:3094-99 (1987)). Weaning from mechanical ventilatory support may be especially difficult during administration of total parenteral nutrition (TPN). The marked increase of $CO_2$ production accompanying the large glucose load of TPN can precipitate respiratory distress. Use of intravenous fat emulsions, which are oxidized with a respiratory quotient of 0.7, (compared to 1.0 for glucose), has been suggested as a means of minimizing $CO_2$ production in patients receiving TPN, especially in patients with compromised respiratory function (Askanazi et al., Anesthesiology 54:373-377 (1981)).

Malnutrition is common in patients with chronic lung disease; 40% of patients with chronic obstructive pulmonary disease (COPD) experience progressive weight loss (Goldstein et al., Clin. Chest Med. 7:141-151 (1986). The development of malnutrition exacerbates the already existing functional impairments of COPD, such as reduced respiratory muscle strength, and decreased diaphragm mass. Therefore a balance must be struck between the aggressive nutritional support required to improve respiratory muscle function and the metabolic demand thus created, which increases the respiratory workload. Goldstein et al. (ibid.) found that refeeding of COPD patients must be performed preventatively, at the start of weight loss. Patients with long term weight loss and end-stage COPD are unable to tolerate increased metabolic demand, and, thus, cannot improve respiratory and skeletal muscle strength through refeeding. An ideal solution to this problem is yet to be found.

In a study examining 6 COPD patients with malnutrition, Suchner et al. (Anesthesiology 6:A421, 1988) found that treatment with GH (30 $\mu$g/day s.c.) in addition to TPN led to no improvement in muscle function, although nitrogen retention and lean body mass still increased. The authors concluded that GH therapy added to TPN may, at least, reduce refeeding-associated complications in COPD patients.

Many patients who fail to wean from the ventilator demonstrate diminished strength of the thoracic and extrathoracic musculature, resulting in poor inspiratory pressure, diminished movement of the thoracic cage, and an inability to insufflate the lungs. Such problems are seen in spinal cord injury patients suffering from quadriplegia, due to acute denervation of thoracic and abdominal muscles. Furthermore, pneumonia and pulmonary emboli frequently complicate the clinical course of quadriplegics during acute recovery from their injury. Progressive weight loss, atrophy of skeletal muscles, and increased nitrogen excretion follow spinal cord transection (Cooper et al. J. Clin. Endocrinol 10:858-870, 1950), with loss of muscle greatest in quadriplegics (Shizgal et al., J. Parent. Ent. Nutr. 10:364-368, 1986). Frequent overfeeding of spinal cord injury patients causes increases in body fat (Greenway et al., Paraplegia 7:301-317, 1970).

In patients without such neurological impairment, use of IMV (Luce et al., Chest 79:678-685, 1981) or nutritional support (Pingleton et al., J.A.M.A. 257:3094-99 (1987); Wilson et al., Am. Rev. Respir. Dis. 131:672-77 (1986)) has led to strengthening of thoracic muscles. Kelly et al., Amer. Rev. Respir. Dis. 130:33-37 (1984), reported a correlation between restoration of lean body mass (through nutritional support) and improvements in pulmonary function.

BRIEF SUMMARY OF THE INVENTION

Recognizing the ongoing need to treat pulmonary dysfunction, particularly pulmonary dysfuntion requiring mechanical ventilatory support, the inventor has developed the following invention. The invention relates to a method of treating pulmonary dysfunction in a mammal comprising administration of growth hormone to said mammal. In one embodiment wherein the pulmonary dysfunction results in ventilator dependency, the use of the method of this invention promotes the withdrawal of mechanical ventilatory support.

BRIEF DESCRIPTION OF THE PREFERRED EMBODIMENTS

The invention is directed to the treatment of respiratory dysfunction in a mammalian subject comprising the administration to said subject of an amount of growth hormone effective to ameliorate, cure, or prevent said pulmonary dysfunction. In one embodiment wherein the pulmonary dysfunction requires ventilatory support, the invention allows earlier removal of the subject from such ventilatory support.

By the term "growth hormone" is intended either natural or recombinant pituitary growth hormone (GH), regardless of the source. The term is limited only in that the material must demonstrate pituitary growth hormone biological activity in a recipient. Therefore, it also applies to physiologically active equivalents, variants with sequence alterations in one or more amino acids, fragments, or portions of the complete GH molecule. Included within the term is naturally-occurring GH which has been isolated from cadavers using techniques well known in the art. Typical techniques for isolation of human GH are disclosed by Lewis et al., U.S. Pat. No. 2,974,088 (1961) and Reisfeld et al., *Endocrinology* 71:559 (1962). Isolation of GH from bovine anterior pituitary is disclosed by Li et al., *J. Biol. Chem.* 159:353 (1945) and Wilhelmi et al., *J. Biol. Chem.* 176:735 (1948). Also included is recobminant GH; preparation of recombinant GH is disclosed by Goeddel et al., *Nature* 281:544–548 (1979). In one embodiment, the recombinant GH includes an additional methionine residue at the N-terminus which is not found on natural GH. In a different embodiment, the recombinant GH may be the "mature" form, i.e., having the same N-terminus as natural GH.

One preferred form of GH of the present invention is human GH. Other preferred forms are recombinant human GH and recombinant human methionyl GH.

The specific amount of GH required by each individual will be dependent upon the age, health, and weight of the recipient, kind of concurrent treatment, if any, frequency of treatment, and the nature of the effect desired. Generally, daily dosages of GH will be from about 0.05 to 0.3 mg per kg of body weight. Normally, from 0.07 to 0.15 mg/kg/d, in one or more applications per day, is effective to obtain the desired result. In an alternative approach, the GH, particularly where formulated in a timed-release form, may be administered less frequently, i.e., every other day or every third day.

The GH treatment of the present invention may be administered by any means, routes, or pharmaceutical compositions that achieve their intended purpose. Amounts and regimens for the administration of GH can be determined readily by those with ordinary skill in the art.

For example, administration may be by parenteral, subcutaneous, intravenous, intramuscular, intrapulmonary, intraperitoneal, intranasal, transdermal, or buccal routes. Alternatively, or concurrently, administration may be by the oral route.

The pharmaceutical composition may be employed in dosage form such as tablets, capsules, powder packets, or liquid solutions, suspensions, or elixirs, for oral administration, or sterile liquid for formulations such as solutions or suspensions for parenteral use. Where the composition is to be administered orally, the GH must be enterically coated in order to prevent gastric digestion or decomposition of the GH. As is known in the art, enteric coatings do not permit release of a significant quantity of the drug until the dosage form passes into the small intestine. Enteric coating compositions are well known to the art and generally may be subdivided into three groups: 1) mixtures of fats and fatty acids; 2) shellac and shellac derivatives; and 3) cellulose acetate phthalates. This last group of compounds are preferred, but any of the enteric coatings known and in common use throughout the pharmaceutical industry are suitable for the practice of this invention.

By the term "respiratory dysfunction" is intended a clinically evident change in any of a number of physiologic parameters associated with normal lung function and respiration in mammals. Such parameters include, but are not limited to: tidal volume, vital capacity, forced expiratory volume, peak inspiratory pressure, spontaneous resting minute ventilation, $VO_2$, $VCO_2$, respiratory quotient, inspiratory muscle strength, lung elasticity, and diaphragm excursion.

By "causes" of said respiratory dysfunction are intended physical injuries or naturally-occurring diseases.

By "physical injuries" are intended any of a number of injuries resulting from, but not limited to, spinal cord injury (quadriplegia, paraplegia, hemiplegia) or surgical intervention. Such injuries may include sternal fractures, rib fractures, flailed chest, diaphragmatic injury, or nerve injury with diaphragmatic paralysis.

By naturally occurring diseases are intended any of a number of diseases, including, but not limited to: pulmonary diseases such as chronic obstructive pulmonary disease, pneumonia and other pneumonitides, asthma, emphysema, tuberculosis; connective tissue disorders such as scleroderma; sepsis; neurological disorders such as stroke, Guillan-Barre Syndrome, demyelinating viral diseases (e.g. poliomyelitis), remote neuromuscular effects of cancer, congenital and other lesions of the spinal cord, diphtheria neuropathy, myasthenia gravis, botulism; drug-induced weakness; muscle dystrophies such as myotonic dystrophy and Duchenne's dystrophy; and chest deformities such as kyphioscoliosis.

The preferred animal subject of the present invention is a mammal. By the term "mammal" is meant an individual belonging to the class Mammalia. The invention is particularly useful in the treatment of human subjects.

By the term "treating" is intended the administering to subjects of GH for purposes which may include prevention, amelioration, or cure of pulmonary dysfunction or assistance in hastening weaning from mechanical ventilation.

EXAMPLE

The following example is illustrative, but not limiting, of the method of use of the present invention. Other suitable modifications and adaptations of the variety of conditions and parameters normally encountered in clinical therapy and which are obvious to those skilled in the art are within the spirit and scope of the invention.

An acute quadriplegic patient who could not be weaned from the ventilator, was treated with growth hormone in an attempt to increase the strength of the diaphragm and accessory respiratory musculature.

Clinical History

A 37 year old male, previously healthy, was admitted to the emergency ward following a fall from a 30 foot ladder, with flaccid extremities and no sensation below the C4-5 level. Radiological findings included a fracture of the spinal cord at the C6-7 level and evidence of a stretch injury at the C4-5 level. The patient's tidal volume was reduced from a normal level of 600-700 ml to about 200 ml. He was intubated and placed on a mechanical ventilator.

On day 24 of hospitalization, following a posterior fusion of the C3-T3 vertebrae, the patient was maintained on mechanical ventilation of 10-12 breaths/min., with a positive end expiratory pressure of 10 cm H$_2$O. Parenteral and enteral feedings were given to provide about 1800-2000 kcal/d., adequate protein and other nutrients. Following further complications, a feeding gastrostomy was inserted on d. 50.

Throughout this period, the patient generated poor inspiratory pressures of $-10$–$15$ cm H$_2$O (normal: $-80$ cm H$_2$O), associated with tidal volumes averaging around 300 ml and vital capacities of about 500 ml (normal: 3000–4000 ml).

Because previous studies had suggested that the administration of GH to catabolic patients increased protein accretion and achieved a positive nitrogen balance, (Ziegler et al., *Ann. Surg.* 206:6-16 (1988)), the patient was determined to be a candidate for this study of GH therapy. The control study week was started on the 62nd hospital day. Recombinant human growth hormone (Protropin) injections of 10 mg/d. subcutaneously were initiated on day 69.

Methods

Basal energy requirements were estimated and a standard liquid feeding formula was administered by gastrostomy to achieve these requirements. Oral feeding was later added. Urine (24 hrs) was collected throughout the study. Vital signs and blood studies were performed as indicated clinically, and, in addition, blood samples were obtained at weekly and later biweekly intervals. Pulmonary functions (inspiratory pressure, tidal volume, and vital capacity) were measured 2-3 times per week.

Urine and blood substrate concentrations were determined using standard techniques. Intake of nitrogen, potassium, and phosphorous were estimated from standard tables of nutrient composition and from the manufacturer's determination of the tube feeding composition. Balance was measured as intake minus output (with stool nitrogen loss assumed to be 1.3 g/d.). Blood and urinary values from each study week were averaged. Data were expressed as mean+SEM, and statistically analyzed with non-paired t tests and ANOVA, where appropriate.

RESULTS

1. Pulmonary Function (Table 1)

During the control week, the patient was on intermittent mandatory ventilation of 6 breaths/min. Measurements of lung mechanics indicated a reduced tidal volume of 200 ml., vital capacity of 425 ml., and an inspiratory pressure of $-19$ cm H$_2$O. Within 3 d. of GH treatment, vital capacity and tidal volume increased, and this response continued over 4 weeks. During the second week, the patient was placed on continuous positive airway pressure (CPAP, 5 cm H$_2$O), and the length of time spontaneous ventilation was tolerated increased gradually. On the third week of GH, diaphragm function improved. Inspiratory pressure rose to levels between $-22$ and $-26$ cm H$_2$O. On the 30th d. of GH treatment the patient was weaned from the ventilator.

2. Metabolism (Table 2)

Food intake remained relatively stable over the first 2 wk. but gradually increased over the last 3 wk., related to an increase in appetite. During the first study week, the patient was in nitrogen equilibrium or slight negative balance. With initiation of GH therapy, a positive nitrogen balance developed promptly and was maintained for the entire study period. Potassium moved from negative to neutral balance. Phosphorous excretion deceased in the first week of GH therapy and then gradually rose as intake increased. The percentage of phosphorous retained during GH was generally increased compared to the control week.

With treatment, concentrations of free fatty acids, glucose, insulin, prealbumin, retinol-binding protein, and transferrin increased. Insulin-like growth factor-1 (IGF-1) levels rose more than 5-fold. These results are shown in Table 3.

Discussion

In patients who fail to wean from the ventilator, it is common to find diminished strength of thoracic and extrathoracic muscles, leading to poor inspiratory pressure, diminished movement of the thoracic cage, and an inability to insufflate the lungs. In this study, these problems were related to denervation of thoracic and abdominal muscles consequent to spinal cord injury. Additional injury to the lungs arose from pneumonia and pulmonary emboli encountered during the first few weeks after injury. Together, these factors did not allow the diaphragm and extrathoracic muscles to compensate for lack of function of the chest wall musculature.

In the quadriplegic patient large muscle loss occurs due to denervation. Energy requirements are concomitantly lower; often these patients are overfed, causing increases in body fat (Cox et al., *J. Trauma* 25:419–423, 1985; Greenway et al., *Paraplegia* 7:301-317, 1970). In the patient of this study, predicted caloric requirements of 1400 kcal/d. were generally exceeded during GH administration. The patient gained 8 kg of body weight during the study. Based on an assumption of a constant energy expenditure of 1400 kcal/d. throughout the study, a positive calorie balance of about 22,000 kcal was calculated during the GH treatment. This could account for 3 kg. of adipose tissue.

The patient gained about 100 g. of nitrogen with GH treatment, representing 625 g of protein, which could account for 2.5 kg of lean tissue. The remaining 2.5 kg of weight gain is attributed to water. This is in line with reports that spinal cord injury patients are susceptible to fluid retention (Greenway et al., *Paraplegia* 7:301-317, 1970) and the slight fluid retention associated with GH treatment (Cox et al., *J. Trauma* 25:419–423, 1985).

Evidence that some of the retained nitrogen, presumably protein, was incorporated into skeletal muscle comes from the finding that creatinine excretion, a common indicator of muscle mass, rose from 457 mg/d during the control period to 814 mg/d during the last week of treatment. This is presumed to be a reflection of the effect of GH on skeletal muscle mass rather than on creatinine metabolism, since similar changes have not been seen in stable patients (without spinal cord injury) getting GH over the same period. The increased retention of potassium and phosphorous, also constituents of skeletal muscle, support this conclusion.

The improvement of tidal volume and vital capacity, and the ability to breathe without mechanical support also indicate an increase in muscle strength. This likely represents an effect of GH on the function of those muscles which have remained innervated. The action of GH, or of IGF-1, on denervated muscle is unknown. IGF-1 is known to exert protein stimulatory effects on cultured cells. It is therefore likely that protein was synthesized in muscle tissue below the site of spinal cord injury.

With this patient, it was speculated at the outset that it would take months to over a year to wean him from the ventilator. The results were therefore dramatic, and argue strongly for this form of therapy as novel approach to wean other ventilator dependent patients.

be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

TABLE 1

| Parameter* | PULMONARY FUNCTION | | | | | |
| --- | --- | --- | --- | --- | --- | --- |
| | Week of Growth Hormone Treatment | | | | | |
| | Control | GH/1 | GH/2 | GH/3 | GH/4 | GH/5 |
| Tidal Volume (cc) | 200 | 410 | 300 | 310 | 334 | 500 |
| Vital Capacity (cc) | 425 | 667 | 600 | 700 | 800 | 750 |
| Inspiratory Pressure (cc $H_2O$) | −19 | −18 | −26 | −22 | −17.3 | — |
| Diaphragmatic Excursion (mm): | | | | | | |
| Left hemidiaphragm | 4 | | | 13 | | |
| Right hemidiaphragm | 25 | | | 36 | | |

*Values represent weekly median. If the patient was sleeping, the tidal volume, vital capacity and inspiratory pressures were not considered for the calculation of the weekly median. If the patient was receiving sleeping drugs, the inspiratory pressure was not considered for the weekly median.

TABLE 2

| Week of Study | Caloric Intake[1] | Nitrogen[2] | | Potassium[3] | | Phosphorous[4] | |
| --- | --- | --- | --- | --- | --- | --- | --- |
| | | Intake | Balance | Intake | Balance | Intake | Excretion |
| Control | 1396 ± 116 | 7.3 ± 0.9 | −1.4 ± 0.8 | 52 ± 6 | −21 ± 7 | 595 ± 64 | 346 ± 74 |
| GH/1 | 1706 ± 180 | 9.7 ± 0.6 | 3.1 ± 0.7 | 61 ± 3 | −10 ± 7 | 772 ± 35 | 242 ± 52 |
| GH/2 | 2195 ± 165 | 12.7 ± 1.1 | 3.7 ± 1.0 | 93 ± 4 | 4 ± 12 | 1149 ± 73 | 437 ± 49 |
| GH/3 | 2055 ± 109 | 11.7 ± 0.6 | 3.3 ± 0.7 | 66 ± 5 | −4 ± 12 | 1065 ± 78 | 650 ± 107 |
| GH/4 | 2251 ± 300 | 12.1 ± 1.6 | 2.6 ± 1.8 | 83 ± 8 | 2 ± 16 | 1127 ± 100 | 695 ± 55 |
| GH/5* | 1956 ± 158 | 14.3 ± 3.5 | 3.6 ± 3 | 65 ± 3 | — | 1150 ± 29 | 1100 ± 66 |

[1] In units of kcal/day.
[2] In units of g/day.
[3] In units of mEq/day.
[4] In units of mg/day.
*3 days only

TABLE 3

| Parameter | METABOLISM | | | | | |
| --- | --- | --- | --- | --- | --- | --- |
| | Week of Growth Hormone Treatment | | | | | |
| | Control | GH/1 | GH/2 | GH/3 | GH/4 | GH/5 |
| Temperature (°C.) | 37.7 | 37.9 | 37.5 | 37.3 | 37.4 | 37.1 |
| Pulse Rate (bpm) | 100 | 115 | 121 | 119 | 115 | 117 |
| Glucose (mg/dl) | 134 | 162 | 174 | 196 | 219 | 133 |
| Blood urea nitrogen (mg/dl) | 5 | 4 | 8 | 6 | 7 | 10 |
| Creatinine (mg/dl) | 0.1 | 0.3 | 0.4 | 0.4 | 0.5 | 0.3 |
| Free fatty acids (μEq/l) | 785 | 1160 | 820 | 990 | — | 955 |
| SGOT (I.U./l) | 87 | 68 | 63 | 33 | 32 | 26 |
| Alkaline Phosphatase (U/l) | 407 | 505 | 1038 | 878 | — | 592 |
| K (μEq/l) | 4.4 | 4.1 | 4.3 | 4.3 | 4.4 | 4.2 |
| $PO_4$ (mg/dl) | 4.3 | 4.0 | 4.3 | 4.8 | 4.5 | 5.1 |
| Albumin (g/dl) | 3.1 | 2.9 | 3.2 | 2.9 | — | 2.9 |
| Prealbumin (mg/dl) | 29.4 | 29.6 | — | 38.1 | — | 37.0 |
| Retinol-binding protein (mg/dl) | 4.6 | 4.5 | — | 7.4 | — | 6.0 |
| Transferrin (mg/dl) | 180 | 203 | — | 237 | — | 357 |
| Insulin (μU/ml) | 32 | 51 | 70 | 74 | 49 | — |
| Growth Hormone (ng/ml) | 1.1 | 1.2 | 4.4 | 6.8 | 2.1 | — |
| IGF-1 (U/ml) | 1.2 | 6.8 | 8.2 | 11.3 | 11.4 | 8.1 |

Therapy of patients with, but not limited to, the above dysfunction, using methods similar to, but not limited to, those used above are the stated objectives of this invention.

Having now fully described this invention, it will be appreciated by those skilled in the art that the same can

I claim:

1. A method for decreasing ventilator dependency which results in hastening the weaning of a patient from a mechanical ventilator in a human comprising administering to a human in need of such treatment a therapeutically effective amount of growth hormone.

2. The method of claim 1, wherein said human growth hormone is produced from recombinant DNA.

3. The method of claim 1, wherein said human growth hormone is recombinant human methionyl growth hormone.

4. The method of claim 1, wherein said effective amount of growth hormone is a dosage in the range of 0.05 to 0.3 mg/kg/day.

5. The method of claim 1, wherein said growth hormone is administered subcutaneously, transdermally, intravenously, orally, nasally, or rectally.

6. The method of claim 1 wherein said ventilator dependency is the result of decreased inspiratory muscle strength.

7. The method of claim 1 wherein said ventilator dependency is the result of decreased lung elasticity.

8. The method of claim 1 wherein said ventilator dependency is the result of physical injury.

9. The method of claim 8 wherein said injury is spinal cord injury.

10. The method of claim 9 wherein said spinal cord injury produces a condition of quadriplegia.

11. The method of claim 8 wherein said injury is a consequence of a surgical procedure.

12. The method of claim 1 wherein said ventilator dependency results from a naturally occurring disease.

13. The method of claim 12 wherein said disease is chronic obstructive pulmonary disease.

14. The method of claim 12, wherein said disease is sepsis.

* * * * *